(12) United States Patent
Lecour et al.

(10) Patent No.: US 6,444,168 B1
(45) Date of Patent: *Sep. 3, 2002

(54) APPARATUS COMPRISING FURNACES, REACTORS OR CONDUITS USED IN APPLICATIONS REQUIRING ANTI-COKING PROPERTIES AND NOVEL STEEL COMPOSITIONS

(75) Inventors: Philipe Lecour, Les Mureaux; Xavier Longaygue, Noisy le Roi; Francois Ropital, Rueil Malmaison, all of (FR)

(73) Assignee: Institu Francais du Petrole (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/676,785

(22) Filed: Oct. 2, 2000

Related U.S. Application Data

(63) Continuation-in-part of application No. 09/282,219, filed on Mar. 31, 1999, now Pat. No. 6,235,238.

(30) Foreign Application Priority Data

Mar. 31, 1998 (FR) .............................................. 98 04088

(51) Int. Cl.[7] .......................... C22C 38/22; C22C 38/34; C22C 38/44
(52) U.S. Cl. ........................... 420/67; 420/69; 420/105; 420/110; 420/111; 420/117; 148/325; 148/334
(58) Field of Search ............................... 420/34, 67, 68, 420/69, 105, 110, 111, 117; 148/325, 334

(56) References Cited

U.S. PATENT DOCUMENTS

| 1,456,088 A | 5/1923 | Armstrong |
| 3,455,681 A | 7/1969 | Moskowitz et al. .......... 75/126 |
| 4,141,724 A | 2/1979 | Brickner et al. .......... 75/126 D |
| 4,790,977 A | 12/1988 | Daniels et al. .............. 420/104 |

FOREIGN PATENT DOCUMENTS

| EP | 0 338 133 | 10/1989 |
| FR | 627.628 | 10/1927 |
| GB | 461 251 | 2/1937 |

*Primary Examiner*—Deborah Yee
(74) *Attorney, Agent, or Firm*—Millen, White, Zelano & Branigan, P.C.

(57) ABSTRACT

In order to produce elements for furnaces, reactors or conduits on the walls of which coke can appear, steels are used with a composition which is adapted to resist coking comprising, by weight, at most 0.25% of C, 1.5% to 5% of Si, 4% to 10% of Cr, 0.5% to 2% of Mo, 0.3% to 1% of Mn, at most 0.030% of S and at most 0.03% of P, the complement to 100% being essentially iron. Novel steel compositions for use in these applications are those which comprise, by weight, at most 0.25% of C, more than 2.5% and up to 5% of Si, 4% to 10% of Cr, 0.5% to 2% of Mo, 0.3% to 1% of Mn, at most 0.03% of S and at most 0.03% of P, the complement to 100% being essentially iron.

31 Claims, 1 Drawing Sheet

APPARATUS COMPRISING FURNACES, REACTORS OR CONDUITS USED IN APPLICATIONS REQUIRING ANTI-COKING PROPERTIES AND NOVEL STEEL COMPOSITIONS

This application is a continuation-in-part application of U.S. patent application Ser. No. 09/282,219, filed Mar. 31, 1999, now U.S. Pat. No. 6,235,238B1 issued May 22, 2001.

BACKGROUND OF THE INVENTION

1. Field of the Invention

The present invention relates to the use of low alloy steels in applications involving anti-coking properties. Such steels are primarily intended for the manufacture of the elements of apparatus such as reactors, furnaces or conduits or for coating such apparatus primarily used in refining processes or in the petrochemicals industry, such steels having an improved resistance to coking.

The invention also relates to novel compositions of such steels with an improved resistance to coking.

The carbonaceous deposit that develops in furnaces when converting hydrocarbons is generally termed coke. This coke deposit is a nuisance in industrial units. The formation of coke on the walls of tubes and reactors causes a reduction in heat exchange, major blockages and thus an increase in pressure drops. In order to keep the reaction temperature constant, it may be necessary to increase the temperature of the walls, which risks damaging the alloy constituting those walls. A reduction in the selectivity of the facilities, and thus a reduction in yield, is also observed

2. Description of the Prior Art

Japanese application JP-A-03/10 4843 describes a refractory anti-coking steel for an ethylene cracking furnace tube. However, that steel comprises more than 15% of chromium and nickel and at least 0.4% of manganese. That steel was developed to limit coke formation between 750° C. and 900° C. when cracking ethylene.

In addition, U.S. Pat. No. 5,693,155 concerns petrochemical processes using low coking stainless steels. Such steel contain at least 10% of nickel and at least 10% of chromium.

SUMMARY OF THE INVENTION

Surprisingly, it has now been discovered that the enrichment in silicon of low alloyed chromium—molybdenum steels has a beneficial effect on the anti-coking properties of said low alloyed steels. Because of the chromium and nickel contents lower than those of the steels disclosed in U.S. Pat. No. 5,693,155, the steels of the present invention are less expensive.

An object of the invention is an apparatus comprising furnaces, reactors or conduits having at least their internal walls, on which coke can appear, composed at least partly of a steel with a composition which is adapted to resist coking comprising, by weight, at most 0.25% of C, 1.5% to 5% of Si, 4% to 10% of Cr, 0.5% to 2% of Mo, 0.3% to 1% of Mn, at most 0.03% of S and at most 0.03% of P, the complement to 100% being essentially iron. Such apparatus are intended for refining or petrochemical processes carried out at temperatures of 350° C. to 1100° C, particularly catalytic naphtha reforming reactions, carried out at temperature, of 450° C. to 650° C. and isobutane dehydrogenation, carried out at temperatures of 550° C. to 700° C.

A further object of the invention is a steel composition for use in these applications comprising, by weight, at most 0.25% of C, more than 2.5% and up to 5% of Si preferably more than 3.1% Si, more than 7% to 10% of Cr, preferably at least 7.1% to less than 10.0%, 0.5% to 2% of Mo, 0.3% to 1% of Mn, at most 0.03% of S and at most 0.03% of P, the complement to 100% being essentially iron.

DETAILED DESCRIPTION OF THE INVENTION

Figure 1:
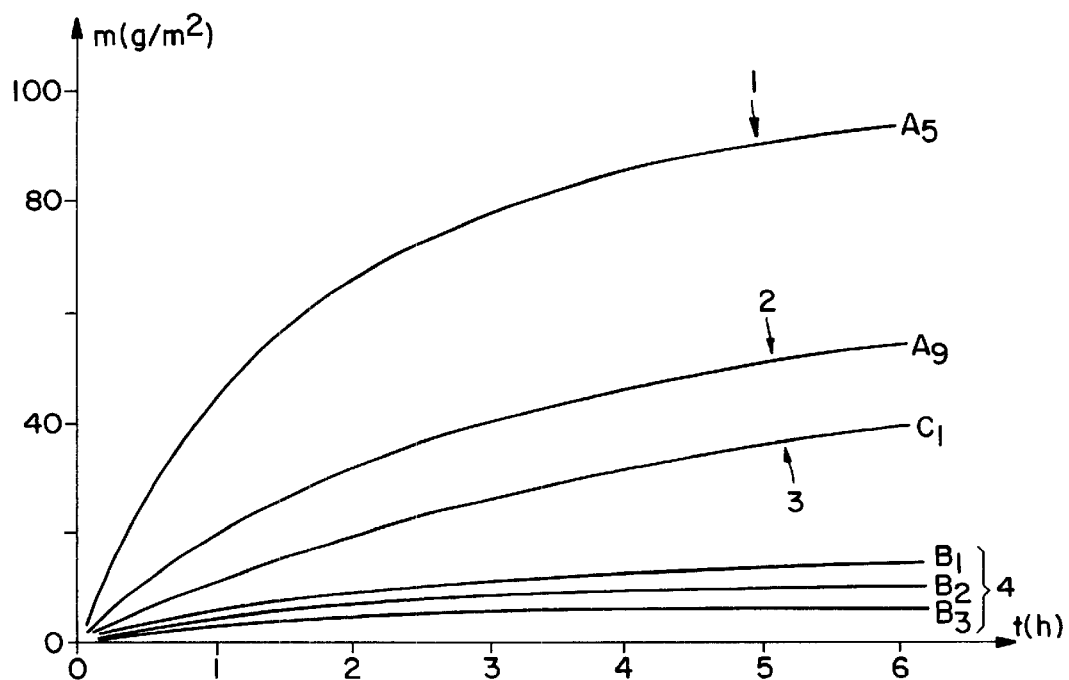
FIG. 1 shows the coking curves for different steels during a catalytic reforming reaction.

In accordance with the invention, an apparatus is provided that has a good resistance to coking and comprises a furnace, a reactor or a conduit at least the internal walls of which are composed of a steel composition comprising:

at most 0.25% of C;

1.5% to 50% of Si, preferably at least 2.5%, and particularly over 3.1% Si;

4% to 10%, preferably more than 7% up to 10% especially over 7.1 or 7.2 or 7.3% up to less than 10.0% of Cr;

0.5% to 2% of Mo;

0.3% to 1% of Mn;

at most 0.03% of S; and at most 0.03% of P;

the complement to 100% being essentially iron.

The steels used in the apparatus of the invention can further comprise:

at most 0.1% of Nb;

at most 0.40% of V;

at most 0.10% of N;

at most 0.05% of Al;

at most 0.4% of Ni; and at most 0.2% of W.

Preferably these steels contain no W. Likewise, steels of the invention do not rely on the incorporation of titanium which would influence the properties of the steel; therefore steels without Ti are preferred.

More particularly, for the apparatus of the invention, use is made of a steel comprising:

about 0.1% of C;

from 1.5 to 3% of Si;

about 9% of Cr;

about 1% of Mo;

about 0.5% of Mn and at most 0.40% of V;

the complement to 100% being essentially iron.

Also for the apparatus of the invention use can particularly be made of a steel comprising:

about 0.1% of C;

more than 3% up to 5% of Si;

about 9% of Cr;

about 1% of Mo;

about 0.5% of Mn and at most 0.40% of V, the complement to 100% being essentially iron.

In accordance with the invention, it is possible to produce some elements intended for the production of furnaces, reactors or conduits in one piece. In such a came the steels can be manufactured using conventional foundry and casting methods, then formed using the usual techniques to produce, for example, sheets, screens, tubes, profiles, ferrules or plates. These semi-finished products can be used to construct the principal parts for furnaces, reactors or conduits, or simply accessory or auxiliary parts thereof.

In the present invention, these steels can also be used in the form of powders to produce coatings on the internal walls of furnaces, reactors or conduits. Thus the internal walls of a furnace, reactor or conduit are coated using at least one technique selected from co-centrifugation, the plasma technique, PVD (Physical Vapor Deposition), CVD (Chemical Vapor Deposition), an electrolytic technique, an overlay technique and plating.

The apparatus or elements produced using steels with the composition defined above can be used in refining or petrochemical processes carried out at temperatures of 350° C. to 1100° C., for example catalytic or thermal cracking and dehydrogenation.

As an example, during catalytic reforming, which produces a reformate at temperatures of 450° C. to 650° C., a secondary reaction causes coke formation. This coke formation is catalytically activated by the presence of nickel, iron and/or their oxides.

A further application can be dehydrogenation of isobutane, which can produce isobutene at temperatures of 550° C. to 700° C.

The invention also relates to novel steels, which can be used in the above applications.

These steel, are generally defined as comprising:
at most 0.25% of C;
more than 2.5% and up to 5% of Si;
more than 7% up to 10% of Cr;
0.5% to 2% of Mo;
0.3% to 1% of Mn;
at most 0.03% of S; and
at most 0.03% of P;
the complement to 100% being essentially iron.
These steels can also comprise:
at most 0.1% of Nb;
at most 0.40% of V;
at most 0.10% of N;
at most 0.05% of Al;
at most 0.4% of Ni; and
at most 0.2% of W.
Preferably these steels contain no W.
In a first variation of the invention, the steel has the following composition:
about 0.1% of C;
more than 2.5% and up to 3% of Si;
about 9% of Cr;
about 1% of Mo;
about 0.5% of Mn;
at most 0.40% of V;
the complement to 100% being essentially iron.
In a further variation of the invention, the steel has the following composition:
about 0.1% of C:
more than 3% to 5% of Si;
about 9% of Cr;
about 1% of Mo;
about 0.5% of Mn;
at most 0.40% of V;
the complement to 100% being essentially iron.

The entire disclosure of all applications, patents and publications, cited above and below, and of corresponding French application 98/04088, filed Mar. 31, 1998, are hereby incorporated by reference.

The invention will be better understood, and its advantages will become clearer from the following non-limiting examples and tests, which are illustrated in the accompanying figures, in which:

The compositions of the steels tested in the following examples are shown in Table 1 below. These steels had a tempered martensitic or bainitic structure.

TABLE 1

| STEELS | C | Si | Mn | Mo | Cr | S | P | V |
|---|---|---|---|---|---|---|---|---|
| A9* | 0.10 | 0.5 | 0.6 | 1.0 | 9.2 | 0.015 | <0.04 | <0.04 |
| A5* | 0.11 | 0.5 | 0.6 | 1.1 | 5.1 | 0.045 | <0.04 | <0.04 |
| B1 | 0.10 | 1.6 | 0.6 | 1.1 | 9.1 | 0.015 | <0.04 | <0.04 |
| B11 | 0.12 | 2.7 | 0.5 | 1.1 | 9.3 | 0.010 | <0.04 | <0.04 |
| B2 | 0.10 | 3.5 | 0.6 | 1.0 | 9.2 | 0.015 | <0.04 | <0.04 |
| B21 | 0.12 | 4.4 | 0.5 | 1.1 | 9.4 | 0.010 | <0.04 | <0.04 |
| B3 | 0.11 | 5 | 0.6 | 1.1 | 9.0 | 0.015 | <0.04 | <0.04 |
| C1 | 0.11 | 1.5 | 0.6 | 1.1 | 5.0 | 0.015 | <0.04 | <0.04 |

*A9 and A5 were standard steels routinely used for the production of furnaces, reactors or reactor elements.

For the tests carried out as described in Examples 1 and 2, the steel samples were prepared as indicated below:
Samples were cut by electro-erosion, then polished with SiC#180 paper to produce a standard surface condition and remove the oxide crust which may to have formed during cutting.
Degreasing was carried out in a $CCl_4$ bath, then in an acetone bath and finally in an ethanol bath.

EXAMPLE 1

The different alloys in Table I were tested in a catalytic naphtha reforming reactor at 600° C., carried out with a hydrogen/hydrocarbon mole ratio of 6/1. The catalytic reforming reaction produced a reformate. A secondary reaction was coke formation. At the temperatures used for that process, the coke deposited was principally constituted by coke of catalytic origin.

The operating procedure used for the tests was as follows:
The samples prepared as described above were suspended on the arms of a thermobalance.
The tube reactor was then closed. The temperature was raised under argon.
The reaction mixture constituted by naphtha, hydrogen and argon was injected into the reactor.
The microbalance continuously measured the weight gain of the sample.

FIG. 1 shows a graph with the time in hours along the abscissa and the weight of coke formed on the sample during the reaction up the ordinate, the weight being given in grams per square meter ($g/m^2$). Curves 1 and 2 relate to steel A5 and A9; curve 3 relates to steel C1; and the curve set 4 relates to steels B1, B2 and B3. The curve corresponding to steel B11 is not shown; it would be placed between the curves corresponding to steels B1 and B2.In the same way, the curve corresponding to steel B21 is not shown it would be placed between the curves corresponding to steels B2 and B3.

It is clear that, for the steel samples of the invention (shown in curve 3 and in the curve set 4), particularly for steels B1, B11, B2, B21 and B3, the degree of coking was reduced with respect to that observed for standard steel samples A5 and A9 (curves 1 and 2).

EXAMPLE 2

A second test was carried out by dehydrogenating isobutane to isobutene at a temperature of about 650° C. and with a hydrogen/hydrocarbon mole ratio of 3/1. The procedure used to prepare the steel samples was that described above and the test procedure was the same as that described in Example 1.

Figure 2:
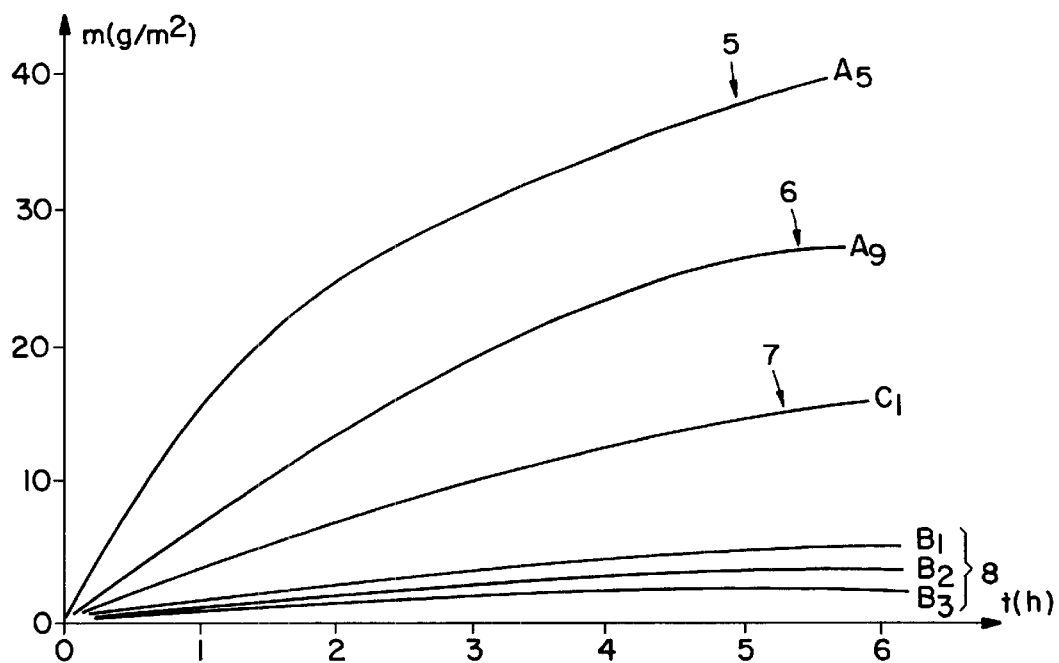
FIG. 2 shows coking curves for different steels for an isobutane dehydrogenation reaction.

FIG. 2 shows that coking of standard steel samples A5 and A9, respectively shown in curves 5 and 6, was substantially higher than coking in steel samples B1, B2 and B3,represented by curve set 8, and to that of steel C1, represented by curve 7. The curve corresponding to steel B11 is not shown; it would be placed between the curves corresponding to steels B1 and B2. In the same way, the curve corresponding to steel B21 is not shown; it would be placed between the curves corresponding to steels B2 and B3.

For this second test, all of the steels of the present invention, which contained silicon, exhibited a lower degree of coking than that of standard steels which did not contain significant proportions of that element.

Finally, the good mechanical characteristics of steels B1, B2 and B3 as well as the ones of steels B11 and B21 of the invention with temperature should be noted. The values measured were about the same for each of the five steels. They are shown in Table 2 below, in which column 1 corresponds to the sample temperature, column 2 to the yield stress, column 3 to the breaking stress, column 4 to the elongation at break and column 5 to the stress to rupture during a creep test after 100000 hours.

TABLE 2

| -1-<br>T<br>(° C.) | -2-<br>Re<br>(MPa) | -3-<br>Rm<br>(MPa) | -4-<br>E<br>(%) | -5-<br>$t_{rup}$<br>100000 (MPa) |
|---|---|---|---|---|
| 500 | 180 | 410 | 40 | 350 |
| 650 | 160 | 390 | 40 | 160 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An apparatus comprising furnaces, reactors or conduits having at least internal walls composed at least partly of a steel comprising:
   at most 0.25% of C;
   1.5% to 5% of Si;
   about 9% of Cr;
   0.5% to 2% of Mo;
   0.3% to 1% of Mn;
   at most 0.03% of S;
   at most 0.03% of P;
   at most 0.2% of W; and
   the complement to 100% being essentially iron.

2. An apparatus according to claim 1, in which the steel further comprises:
   at most 0.1% of Nb;
   at most 0.40% of V;
   at most 0.10% of N;
   at most 0.05% of Al; and
   at most 0.4% of Ni.

3. An apparatus according to claim 1, in which the steel comprises:
   about 0.1% of C;
   1.5% to 3% of Si
   about 1% of Mo;
   about 0.5% of Mn; and
   at most 0.40% of V;
   the complement to 100% being essentially iron.

4. An apparatus according to claim 1, in which the steel comprises:
   about 0.1% of C;
   more than 3% to 5% of Si;
   about 1% of Mo;
   about 0.5% of Mn; and
   at most 0.40% of V;
   the complement to 100% being essentially iron.

5. An apparatus comprising furnaces, reactors or conduits having at least internal walls composed at least partly of a steel comprising:
   0 to 0.25% of C;
   1.5% to 5% of Si;
   more than 7% to 10% of Cr;
   0.5% to 2% of Mo;
   0.3% to 1% of Mn;
   0 to 0.03% of S;
   0 to 0.03% of P; and
   the complement to 100% being essentially iron.

6. An apparatus according to claim 5, wherein chromium is present in a concentration of more than 7.1% to 10%.

7. An apparatus according to claim 5, wherein chromium is present in a concentration of about 9% to 10%.

8. An apparatus according to claim 5, in which the whole furnace, reactor or conduit is composed of said steel.

9. A method of producing an apparatus, comprising coating with the steel according to claim 5 the internal walls of a furnace, reactor or conduit using at least one of co-centrifugation, the plasma technique, PVD (Physical Vapor Deposition), CVD (Chemical Vapor Deposition), an electrolytic technique, or an overlay technique and plating.

10. A steel comprising:
    at most 0.25% of C;
    more than 2.5% and up to 5% of Si;
    more than about 7% to 10% of Cr;
    0.5% to 2% of Mo;
    0.3% to 1% of Mn;
    at most 0.030% of S; and
    at most 0.03% of P:
    the complement to 100% being essentially iron.

11. A steel according to claim 10, further comprising:
    at most 0.1% of Nb;
    at most 0.40% of V;
    at most 0.10% of N;

at most 0.05% of Al;
at most 0.49% of Ni; and
at most 0.2% of W.

12. A steel according to claim 11, comprising:
about 0.1% of C;
more than 2.5% up to 3% of Si;
about 9% of Cr;
about 1% of Mo;
about 0.5% of Mn;
at most 0.40% of V; and
the complement to 100% being essentially iron.

13. A steel according to claim 11, comprising:
about 0.1% of C;
more than 3% to 5% of Si;
about 9% of Cr;
about 1% of Mo;
about 0.5% of Mn;
at most 0.40% of V; and
the complement to 100% being essentially iron.

14. An apparatus comprising furnaces, reactors or conduits having internal walls comprising at least partly of a steel consisting of:
0–0.25% of C;
1.5% to 5% of Si;
above 7.1% to 10% of Cr;
0.5% to 2% of Mo;
0.3% to 1% of Mn;
0–0.03% of S;
0 to 0.03% of P;
0 to 0.1% of Nb;
0 to 0.40% of V;
0 to 10% of N;
0 to 0.05% of Al;
0 to 0.4% of Ni; and
the compliment to 100% being iron.

15. An Apparatus according to claim 5, wherein chromium is present in a concentration of above 7.1% to less than 10.0%.

16. A steel consisting essentially of:
0–0.25% of C:
2.5% to 5% of Si:
above 7.1% to less than 10% of Cr:
0.5% to 2% of Mo:
0.3% to 1% of Mn:
0–0.03% of S:
0 to 0.03% of P:
0 to 0.1% of Nb:
0 to 0.40% of V:
0 to 0.10% of N:
0 to 0.05% of Al:
0 to 0.4% of Ni; and at most 0.2% of W
the compliment to 100% being iron.

17. In a process of conducting a refining or petrochemical process in apparatus wherein the process is carried out at temperatures of 350° C. to 1100° C., the improvement wherein the apparatus is according to claim 5.

18. A process according to claim 17, said process comprising a catalytic naphtha reforming reaction, carried out at temperatures of 450° C. to 650° C.

19. A process according to claim 17, said process comprising isobutane dehydrogenation, carried out at temperatures of 550° C. to 700° C.

20. An apparatus according to claim 2, in which the whole furnace, reactor or conduit is composed of said steel.

21. A method of producing an apparatus, comprising coating with the steel according to claim 2, the internal walls of a furnace, reactor or conduit using at least one of co-centrifugation, the plasma technique, PVD (Physical Vapor Deposition), CVD (Chemical Vapor Deposition), an electrolytic technique, an overlay technique and plating.

22. In a process of conducting a refining or petrochemical process in apparatus wherein the process is carried out at temperatures of 350° C. to 1100° C., the improvement wherein the apparatus is according to claim 2.

23. A process according to claim 22, said process comprising a catalytic naphtha reforming reaction, carried out at temperatures of 450° C. to 650° C.

24. A process according to claim 23, said process comprising isobutane dehydrogenation, carried out at temperatures of 550° C. to 700° C.

25. A steel according to claim 16, wherein chromium is present in a concentration of above 7.2% to less than 10.0%.

26. A steel according to claim 16, wherein chromium is present in a concentration of above 7.3% to less than 10.0%.

27. An apparatus according to claim 1, wherein the steel consists essentially of:
at most 0.25% of C;
1.5% to 5% of Si;
about 9% of Cr;
0.5% to 2% of Mo;
0.3% to 1% of Mn;
at most 0.03% of S;
at most 0.03% of P;
at most 0.2% of W;
at most 0.1% of Nb;
at most 0.40% of V;
at most 0.10% of N;
at most 0.05% of Al;
at most 0.4% of Ni; and
the complement to 100% being essentially iron.

28. An apparatus according to claim 1, wherein the steel consists of:
at most 0.25% of C;
1.5% to 5% of Si;
about 9% of Cr;
0.5% to 2% of Mo;
0.3% to 1% of Mn;
at most 0.03% of S;
at most 0.03% of P;
at most 0.2% of W;
at most 0.1% of Nb;
at most 0.40% of V;
at most 0.10% of N;
at most 0.05% of Al;
at most 0.4% of Ni; and
the complement to 100% being essentially iron.

29. An apparatus according to claim 1, wherein the steel comprises 9% of Cr.

30. An apparatus according to claim 5, wherein the steel consists essentially of:
- 0 to 0.25% of C;
- 1.5% to 5% of Si;
- more than 7% to 10% of Cr;
- 0.5% to 2% of Mo;
- 0.3% to 1% of Mn;
- 0 to 0.03% of S;
- 0 to 0.03% of P;
- 0 to 0.1% of Nb;
- 0 to 0.40% of V;
- 0 to 0.5% of N;
- 0 to 0.5% of Al;
- 0 to 0.4% of Ni; and
- the complement to 100% being essentially iron.

31. An apparatus according to claim 5, wherein the steel further comprises:
- 0 to 0.1% of Nb;
- 0 to 0.40% of V;
- 0 to 0.10% of N;
- 0 to 0.05% of Al;
- 0 to 0.4% of Ni; and
- the complement to 100% being essentially iron.

* * * * *